United States Patent

Nielsen

(10) Patent No.: US 11,137,466 B2
(45) Date of Patent: Oct. 5, 2021

(54) SPIN ECHO MR IMAGING

(71) Applicant: KONINKLIJKE PHILIPS N.V., Eindhoven (NL)

(72) Inventor: Tim Nielsen, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 303 days.

(21) Appl. No.: 15/535,098

(22) PCT Filed: Dec. 11, 2015

(86) PCT No.: PCT/EP2015/079333
§ 371 (c)(1),
(2) Date: Jun. 12, 2017

(87) PCT Pub. No.: WO2016/096623
PCT Pub. Date: Jun. 23, 2016

(65) Prior Publication Data
US 2017/0350954 A1    Dec. 7, 2017

(30) Foreign Application Priority Data

Dec. 15, 2014  (EP) .................... 14197935

(51) Int. Cl.
*G01R 33/561* (2006.01)
*G01R 33/50* (2006.01)
(Continued)

(52) U.S. Cl.
CPC .......... *G01R 33/5613* (2013.01); *A61B 5/055* (2013.01); *G01R 33/50* (2013.01); *G01R 33/56563* (2013.01)

(58) Field of Classification Search
CPC ................ G01R 33/5613; G01R 33/50; G01R 33/56563; A61B 5/055
See application file for complete search history.

(56) References Cited

U.S. PATENT DOCUMENTS 4,792,758 A    12/1988  Sattin
5,818,229 A *  10/1998  Kanazawa ....... G01R 33/56554
                                                      324/309

(Continued)

FOREIGN PATENT DOCUMENTS

CN    104166111 A    11/2014

OTHER PUBLICATIONS

Lee et al "Fast SSFP Gradient Echo Sequence for Simultaneous Acquisitions of FID and Echo Signals" Magnetic Resonance in Medicine, vol. 8, No. 2, Oct. 1, 1988 p. 142-150.

(Continued)

*Primary Examiner* — Patrick Assouad
*Assistant Examiner* — Haidong Zhang

(57) ABSTRACT

MR imaging comprising the steps of: subjecting an object (10) to an imaging sequence of RF pulses and switched magnetic field gradients (GS, GP, GM), which imaging sequence is a steady state sequence comprising a plurality of repeatedly applied acquisition blocks (21), wherein each acquisition block (21) comprises two units (22, 23) in immediate succession, namely: i) a first unit (22) starting with an excitation RF pulse radiated toward the object (10), with the duration of the first unit being an integer multiple of a given time interval T, and ii) a second unit (23) starting with a refocusing RF pulse radiated toward the object (10) and comprising a readout magnetic field gradient (GM) and a phase encoding magnetic field gradient (GP), with the duration of the second unit (23) being an integer multiple of the time interval T, acquiring one or more phase-encoded spin echo signals (31, 32) in a sequence of acquisition blocks (21), and reconstructing one or more MR images from the acquired spin echo signals (31, 32). Moreover, the invention relates to a MR device (1) and to a computer program for a MR device (1).

29 Claims, 2 Drawing Sheets

(51) Int. Cl.
*A61B 5/055* (2006.01)
*G01R 33/565* (2006.01)

(56) References Cited

U.S. PATENT DOCUMENTS

| | | | |
|---|---|---|---|
| 6,239,597 B1 | 5/2001 | McKinnon | |
| 7,834,625 B2 | 11/2010 | Doyle et al. | |
| 9,551,770 B1* | 1/2017 | Nasiraei Moghaddam | ................. G01R 33/4806 |
| 2003/0137298 A1* | 7/2003 | Yamazaki | .......... G01R 33/5613 324/309 |
| 2004/0140803 A1 | 7/2004 | Deimling | |
| 2012/0242334 A1* | 9/2012 | Bieri | ................. G01R 33/5614 324/309 |
| 2013/0089271 A1* | 4/2013 | Boernert | ................ G01N 24/08 382/274 |
| 2014/0210471 A1 | 7/2014 | Stemmer | |

OTHER PUBLICATIONS

Krug et al "Fully Balanced Steady-State 3D Spin Echo (BSSSE) Imaging at 3 Tesla" Magnetic Resonance in Medicine vol. 56, p. 1033-1040 (2006).

Scheffler "A Pictorial Description of Steady-States in Rapid Magnetic Resonance Imaging" Concepts in Magnetic Resonance, vol. 11 (5) p. 291-304 (1999).

Vasilic et al K-Space Analysis and Correction of a Coherence-Induced Artifact in 3D Fast-Large-Angle Spin Echo (Flase) Proc. Intl. Soc. Mag. Reson. Med 11 (2004) p. 100.

Vasilic et al "Coherence Induced Artifacts in Large-Flip Angle Steady State Spin Echo Imaging" Magnetic Resonance in Medicine 52: p. 346-353 (2004).

\* cited by examiner

SPIN ECHO MR IMAGING

CROSS REFERENCE TO RELATED APPLICATIONS

This application is a U.S. national phase application of International Application No. PCT/EP2015/079333, filed on Dec. 11, 2015, which claims the benefit of EP Application Serial No. 14197935.1 filed on Dec. 15, 2014 and is incorporated herein by reference.

FIELD OF THE INVENTION

The invention relates to the field of magnetic resonance (MR) imaging. It concerns a method of MR imaging of an object. The invention also relates to a MR device and to a computer program to be run on a MR device.

BACKGROUND OF THE INVENTION

Image-forming MR methods which utilize the interaction between magnetic fields and nuclear spins in order to form two-dimensional or three-dimensional images are widely used nowadays, notably in the field of medical diagnostics, because for the imaging of soft tissue they are superior to other imaging methods in many respects, do not require ionizing radiation and are usually not invasive.

According to the MR method in general, the body of the patient to be examined is arranged in a strong, uniform magnetic field ($B_0$ field) whose direction at the same time defines an axis (normally the z-axis) of the co-ordinate system on which the measurement is based. The magnetic field produces different energy levels for the individual nuclear spins in dependence on the magnetic field strength. Transitions between these energy levels can be excited (spin resonance) by application of an electromagnetic alternating field (RF field, also referred to as $B_1$ field) of defined frequency (so-called Larmor frequency, or MR frequency). From a macroscopic point of view the distribution of the individual nuclear spins produces an overall magnetization which can be deflected out of the state of equilibrium by application of an electromagnetic pulse of appropriate frequency (RF pulse) while the magnetic field extends perpendicular to the z-axis, so that the magnetization performs a precessional motion about the z-axis. The precessional motion describes a surface of a cone whose angle of aperture is referred to as flip angle. The magnitude of the flip angle is dependent on the strength and the duration of the applied electromagnetic pulse. In the case of a so-called 90° pulse, for example, the spins are deflected from the z axis to the transverse plane (flip angle 90°.

After termination of the RF pulse, the magnetization relaxes back to the original state of equilibrium, in which the magnetization in the z direction is built up again with a first time constant $T_1$ (spin lattice or longitudinal relaxation time), and the magnetization in the direction perpendicular to the z direction relaxes with a second time constant $T_2$ (spin-spin or transverse relaxation time). The variation of the magnetization can be detected by means of one or more receiving RF coils which are arranged and oriented within an examination volume of the MR device in such a manner that the variation of the magnetization is measured in the direction perpendicular to the z-axis. The decay of the transverse magnetization is accompanied, after application of, for example, a 90° pulse, by a transition of the nuclear spins (induced by local magnetic field inhomogeneities) from an ordered state with the same phase to a state in which all phase angles are uniformly distributed (dephasing). The dephasing can be compensated by means of a refocusing pulse (for example a 180° pulse). This produces an echo signal (spin echo) in the receiving coils.

In order to realize spatial resolution in the body, linear magnetic field gradients extending along the three main axes are superposed on the uniform magnetic field, leading to a linear spatial dependency of the spin resonance frequency. The signal picked up in the receiving coils then contains components of different frequencies which can be associated with different locations in the body. The MR signal data obtained via the RF coils corresponds to the spatial frequency domain and is called k-space data. The k-space data usually includes multiple lines acquired with different phase encoding. Each line is digitized by collecting a number of samples. A set of k-space data is converted to a MR image by means of Fourier transformation.

MR imaging in situations, in which a significant inhomogeneity of the main magnetic field is present (for example in inhomogeneous tissue environments or near air/tissue interfaces), is preferably performed by spin echo-type imaging sequences. Compared to gradient echo sequences, they are less sensitive to signal loss arising from magnetic field inhomogeneity. On the other hand, practical considerations, such as shorter scan times and higher signal-to-noise ratios (SNRs), make the use of fast gradient sequences (also referred to as fast field echo or FFE sequences), very attractive. These sequences repeat one basic acquisition block (the duration of which determines the repetition time TR of the sequence) very rapidly while the phase-encoding is varied. Additionally, with recent improvements in the hardware for generating the magnetic field gradients, rapid FFE sequences with very short repetition time ($TR \ll T_2$) and fully balanced gradients over one TR have become very popular for clinical applications. These sequences are commonly known as fully balanced steady-state free precession (bSSFP) sequences. However, these sequences are very sensitive to field inhomogeneity. The resulting images show banding artifacts or signal loss due to intra-voxel dephasing in the presence of inhomogeneities of the main magnetic field.

Spin echo-type imaging sequences are slower than field echo sequences because spin echo sequence cannot be repeated as quickly. On the other hand, spin echo imaging is still required and widely used because it has the advantage of being resistant against main magnetic field inhomogeneity. The U.S. Pat. No. 6,239,597 relates to a magnetic resonance imaging method to rapidly acquire $T_2$-weighted images. To that end, the known acquisition sequence has successive RF pulses of a fixed or varying flip angle the maintain a steady state magnetisation. Data acquisition periods are arranged having centres offset by equal amounts after a first RF pulses and before a next RF pulse, respectively. This achieves control of the ratio of $T_1/T_2$ weighting,

SUMMARY OF THE INVENTION

From the foregoing it is readily appreciated that there is a need for an improved spin echo-based MR imaging technique In accordance with the invention, a method of MR imaging of an object placed in the examination volume of a MR device is disclosed. The method comprises the steps of:

subjecting the object to an imaging sequence of RF pulses and switched magnetic field gradients, which imaging sequence is a steady state sequence comprising a plurality of repeatedly applied acquisition blocks, wherein each acquisition block comprises two units in immediate succession, namely:

i) a first unit starting with an excitation RF pulse radiated toward the object (10), with the duration of the first unit being an integer multiple of a given time interval T, and ii) a second unit starting with a refocusing RF pulse radiated toward the object (10) and comprising a readout magnetic field gradient and a phase encoding magnetic field gradient, with the duration of the second unit being in integer multiple of the same time interval T, acquiring a plurality of differently phase-encoded spin echo signals in a sequence of acquisition blocks, and reconstructing one or more MR images from the acquired spin echo signals. The imaging sequence of the invention consists of two building units, the first and the second unit, which are applied alternately. A combination of the first and second unit applied in immediate succession, i.e. without temporal delay between the two units, constitutes one acquisition block. The imaging sequence repeats this basic acquisition block rapidly (for example with a repetition time of less than 20 ms) while the phase-encoding is varied according to the required k-space sampling. Each unit comprises one RF pulse that excites/refocuses the magnetization of the respective imaging slice (or volume). The durations of the first and second unit are integer multiples of a given time interval T of the imaging sequence respectively. The repetition time is the combined duration of both units.

In order to produce the spin echo signals, the temporal integrals of the magnetic field gradients causing dephasing and rephasing of the transverse magnetization during the first and second units respectively have to correspond to each other so as to achieve refocusing. Additional magnetic field gradients ("crusher gradients") may be applied to suppress free induction decay signals (FIDs) associated with the excitation and refocusing RF pulses. The temporal integral of the magnetic field gradient should the same over each interval T of the acquisition block. This applies to the magnetic field gradients applied in all (three) spatial directions independently, except the phase-encoding magnetic field gradients that are typically applied in a fully balanced fashion.

The proposed imaging sequence is a spin echo sequence which is inherently unsusceptible to main magnetic field inhomogeneity. However, in contrast to conventional spin echo sequences it is a steady state sequence such that it can be used for fast imaging with a high repetition rate (of less than 100 ms, typically less than 20 ms). This renders the technique of the invention especially useful for 3D imaging as well as for dynamic imaging.

Within the meaning of the invention the term "steady state" implies that a non-zero steady state develops for both components of the nuclear magnetization (transverse and longitudinal). The repetition time of the imaging sequence is shorter than both $T_1$ and $T_2$ times of the imaged object. The magnetization never completely decays. The RF pulses and the switched magnetic field gradients of the imaging sequence maintain the steady state of the magnetization over an infinite number of repetitions.

In a preferred embodiment, the excitation and refocusing RF pulses each have a flip angle of 20°-90°, preferably 50°, while the phase difference between the excitation RF pulse and the refocusing RF pulse is at least 30°, preferably at least 50°. With these parameters, the amplitude of the acquired spin echo signals and, thus, the SNR can be maximized. An advantage of the method of the invention over conventional spin echo imaging is that the imaging sequence does not require RF pulses with large flip angles (e.g. 90°/180° combinations like in turbo spin echo sequence). This significantly reduces RF energy deposition in the examined object. Notably, acquiring one or more phase-encoded spin echo signals (31, 32) in a sequence of acquisition blocks (21), is done such that at least one spin echo signal is acquired in any of the first or second unit at an integer number of the time interval T after the refocusing pulse and an integer number before either the end of said first or second unit or next spin echo signal acquired in said first or second unit.

In a further preferred embodiment of the invention, at least two spin echo signals are acquired during the second unit. Two or more spin echoes can be generated according to the method of the invention by selecting the ratio of the durations of the first and second unit accordingly. For example, it is possible to generate two spin echoes during each second unit by selecting a ratio of the duration of the first and second unit of 1:3 or 2:3. The different "families" of echo signals will depend differently on the object's magnetization properties ($T_1$, $T_2$). Hence, the resulting MR images will have different contrast properties. This may be used for deriving quantitative $T_1/T_2$ maps.

In yet another preferred embodiment, the first unit further comprises a switched readout magnetic field gradient, with a gradient echo signal being acquired during the first unit. Appropriate gradient switching during the first unit enables the combined acquisition of gradient and spin echo signals. MR images having different contrast may be reconstructed from the gradient and spin echo signals respectively.

In still another preferred embodiment, the flip angles of the RF excitation and refocusing pulses are varied in the sequence of acquisition blocks. Acquisition blocks with different sets of flip angles and/or phases of the RF pulses may be combined in the imaging sequences. MR images attributed to different sets of flip angles may then be reconstructed from the acquired spin echo signals. This may be used, for example, for parameter mapping in order to establish optimized sequence parameters for the respective imaging task.

The method of the invention described thus far can be carried out by means of a MR device including at least one main magnet coil for generating a uniform steady magnetic field within an examination volume, a number of gradient coils for generating switched magnetic field gradients in different spatial directions within the examination volume, at least one RF coil for generating RF pulses within the examination volume and/or for receiving MR signals from a body of a patient positioned in the examination volume, a control unit for controlling the temporal succession of RF pulses and switched magnetic field gradients, and a reconstruction unit for reconstructing MR images from the received MR signals. The method of the invention is preferably implemented by a corresponding programming of the reconstruction unit and/or the control unit of the MR device.

The methods of the invention can be advantageously carried out in most MR devices in clinical use at present. To this end it is merely necessary to utilize a computer program by which the MR device is controlled such that it performs the above-explained method steps of the invention. The computer program may be present either on a data carrier or be present in a data network so as to be downloaded for installation in the control unit of the MR device.

BRIEF DESCRIPTION OF THE DRAWINGS

The enclosed drawings disclose preferred embodiments of the present invention. It should be understood, however, that the drawings are designed for the purpose of illustration only and not as a definition of the limits of the invention. In the drawings.

DETAILED DESCRIPTION OF THE EMBODIMENTS

Figure 1:
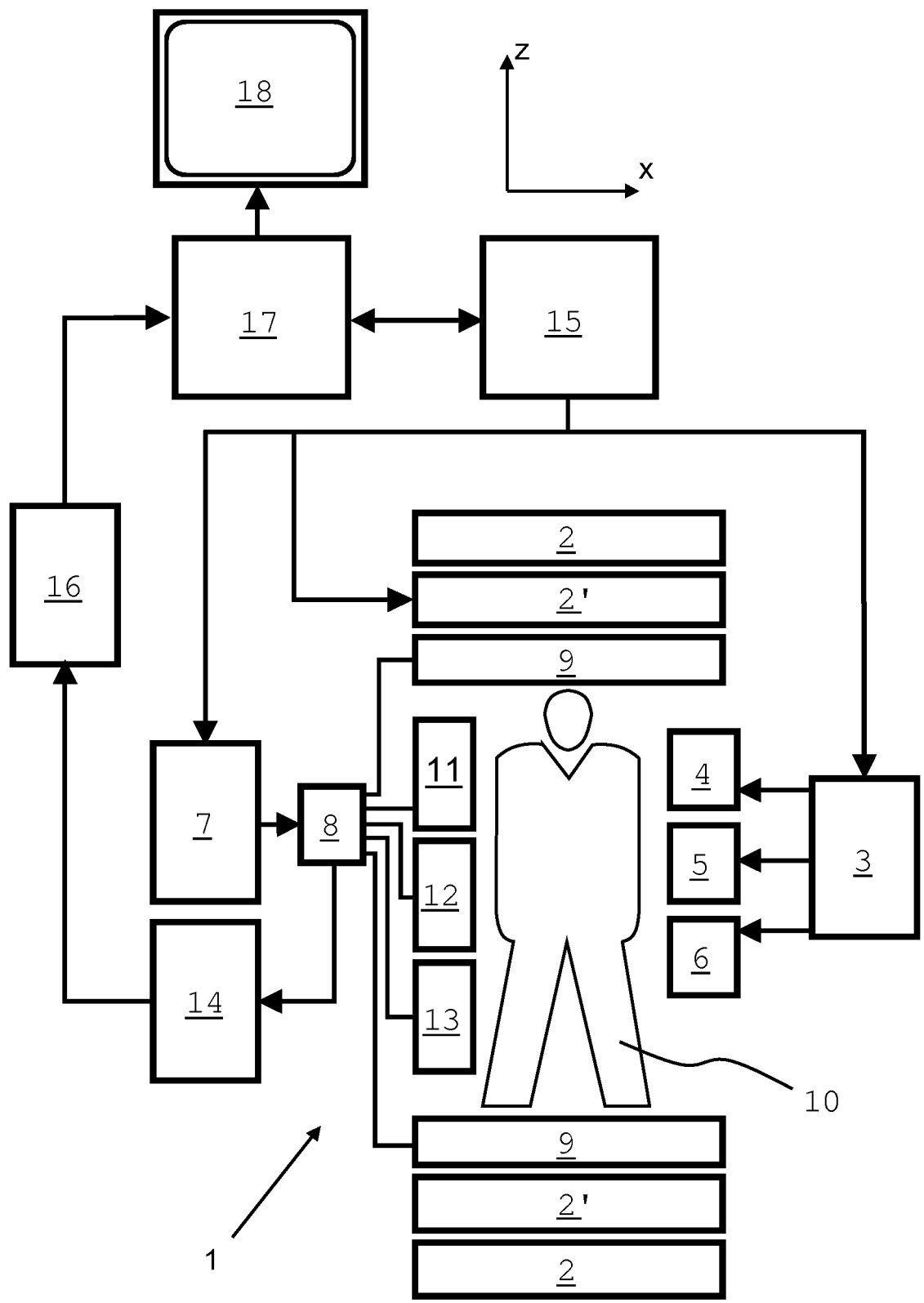
FIG. 1 schematically shows a MR device for carrying out the methods of the invention.

With reference to FIG. 1, a MR device 1 is shown. The device comprises superconducting or resistive main magnet coils 2 such that a substantially uniform, temporally constant main magnetic field $B_0$ is created along a z-axis through an examination volume. The device further comprises a set of ($1^{st}$, $2^{nd}$, and—where applicable—$3^{rd}$ order) shimming coils 2', wherein the current flow through the individual shimming coils of the set 2' is controllable for the purpose of minimizing $B_0$ deviations within the examination volume.

A magnetic resonance generation and manipulation system applies a series of RF pulses and switched magnetic field gradients to invert or excite nuclear magnetic spins, induce magnetic resonance, refocus magnetic resonance, manipulate magnetic resonance, spatially and otherwise encode the magnetic resonance, saturate spins, and the like to perform MR imaging.

Most specifically, a gradient pulse amplifier 3 applies current pulses to selected ones of whole-body gradient coils 4, 5 and 6 along x, y and z-axes of the examination volume. A digital RF frequency transmitter 7 transmits RF pulses or pulse packets, via a send-/receive switch 8, to a body RF coil 9 to transmit RF pulses into the examination volume. A typical MR imaging sequence is composed of a packet of RF pulse segments of short duration which taken together with each other and any applied magnetic field gradients achieve a selected manipulation of nuclear magnetic resonance. The RF pulses are used to saturate, excite resonance, invert magnetization, refocus resonance, or manipulate resonance and select a portion of a body 10 positioned in the examination volume. The MR signals are also picked up by the body RF coil 9.

For generation of MR images of limited regions of the body 10 by means of parallel imaging, a set of local array RF coils 11, 12, 13 are placed contiguous to the region selected for imaging. The array coils 11, 12, 13 can be used to receive MR signals induced by body-coil RF transmissions. In parallel transmit applications, the array RF coils 11, 12, 13 may also be used for RF transmission, for example for the purpose of RF shimming.

The resultant MR signals are picked up by the body RF coil 9 and/or by the array RF coils 11, 12, 13 and demodulated by a receiver 14 preferably including a preamplifier (not shown). The receiver 14 is connected to the RF coils 9, 11, 12 and 13 via send-/receive switch 8.

A host computer 15 controls the current flow through the shimming coils 2' as well as the gradient pulse amplifier 3 and the transmitter 7 to generate the imaging sequence of the invention. The receiver 14 receives a single or a plurality of MR data lines in rapid succession following each RF excitation pulse. A data acquisition system 16 performs analog-to-digital conversion of the received signals and converts each MR data line to a digital format suitable for further processing. In modern MR devices the data acquisition system 16 is a separate computer which is specialized in acquisition of raw image data.

Ultimately, the digital raw image data is reconstructed into an image representation by a reconstruction processor 17 which applies a Fourier transform or other appropriate reconstruction algorithms, such like SENSE or SMASH. The MR image may represent a planar slice through the patient, an array of parallel planar slices, a three-dimensional volume, or the like. The image is then stored in an image memory where it may be accessed for converting slices, projections, or other portions of the image representation into appropriate format for visualization, for example via a video monitor 18 which provides a man-readable display of the resultant MR image.

Figure 2:
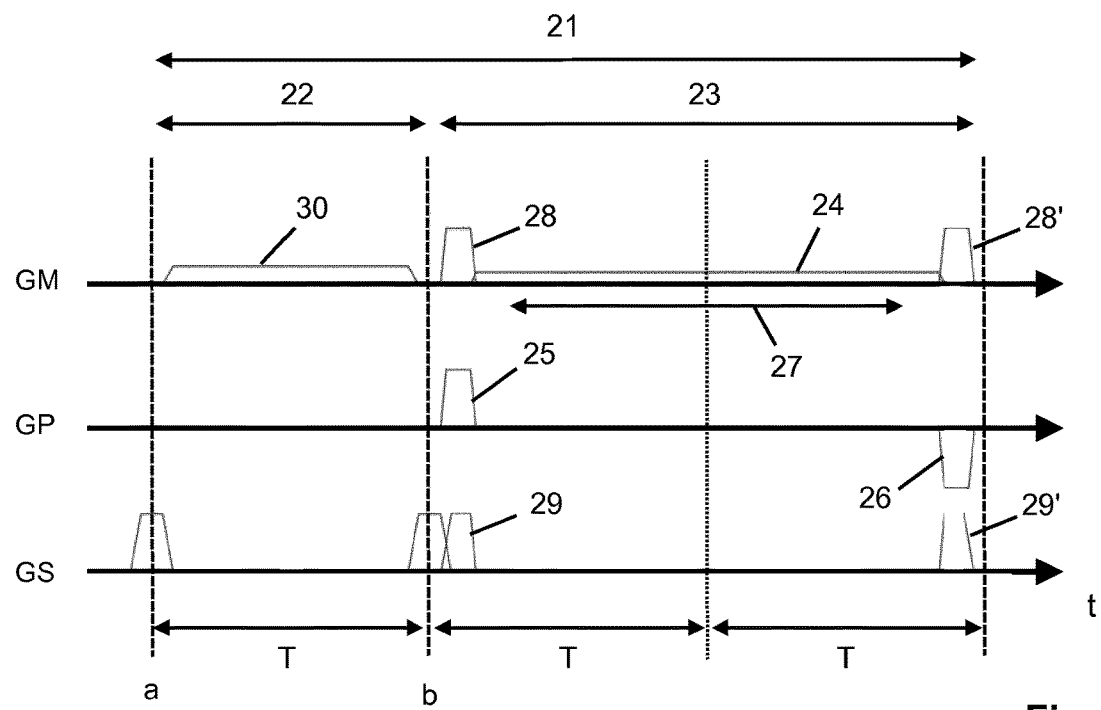
FIG. 2 shows a diagram illustrating the imaging sequence according to the invention.

FIG. 2 shows a diagram illustrating an embodiment of the imaging sequence according to the invention. The magnetic field gradients GS (slice selection), GP (phase encoding), and GM (frequency encoding) are shown as a function of time t. The imaging sequence is a steady state sequence in which a basic acquisition block 21 is rapidly repeated without temporal delay between the repetitions. The acquisition block 21 comprises two units 22, 23 in immediate succession, namely a first unit 22 starting with an excitation RF pulse (not shown) radiated at point a. The duration of the first unit 22 equals the echo time TE of the depicted sequence. The second unit 23 starts with a refocusing RF pulse (not shown) at point b and comprises a readout magnetic field gradient 24 as well as a phase encoding magnetic field gradient 25. The phase encoding gradient 25 is balanced by a corresponding negative gradient pulse 26 at the end of the second unit 23. The duration of the second unit 23 is twice a given time interval T (which equals the echo time TE) in the depicted embodiment. The repetition time of the imaging sequence is the combined duration of the first and second units 22, 23, which is three times the time interval T. The phase-encoding is varied from repetition to repetition of the acquisition block 21 and correspondingly phase-encoded spin echo signals are acquired in the sequence of acquisition blocks 21. The interval during which MR signal acquisition takes place is designated by 27 in FIG. 2. Additional gradients 28, 28', 29, 29' are applied to suppress FID signals. Further, a gradient 30 is applied during the first unit 22. The temporal integral of the magnetic field gradient GM over the first half of the second unit 23 equals the temporal integral of the magnetic field gradient GM over the first unit 22. Likewise, the temporal integral of the magnetic field gradient GM over the second half of the second unit 23 equals the temporal integral of the magnetic field gradient GM over the first unit 22. The temporal integral of the magnetic field gradient GM is the same for each interval T, which is essential for the steady state imaging sequence of the invention because it ensures that spin echoes are formed at all integer multiples of T. This condition should be fulfilled for all gradient channels GS, GP, GM independently, wherein the variable phase-encoding magnetic field gradients are not taken into account. The phase-encoding is fully "rewound" (balanced). The temporal gradient integrals applied during the first and second units 22, 23 respectively correspond to each other such that refocusing of the spin echo signal is achieved in the middle of the second unit 23 in the depicted embodiment. Finally, a MR image is reconstructed from the spin echo signals acquired during the repetitions of the acquisition block 21.

Figure 3:
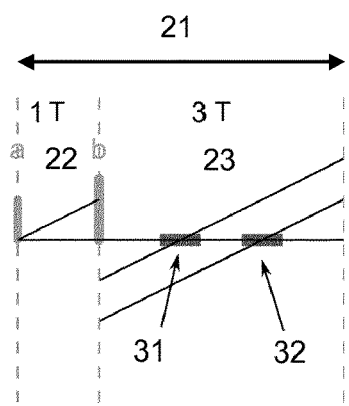
FIG. 3 schematically shows an embodiment of the invention in which two spin echoes are generated during one acquisition block.

In the variant shown in FIG. 3, two spin echoes 31, 32 are generated during the second unit 23. The inclined solid lines in the diagram schematically indicate the phase evolution of the transverse magnetization under the applied magnetic field gradients. The ratio of the durations of the first and second units 22, 23 is 1:3 in this embodiment.

Figure 4:
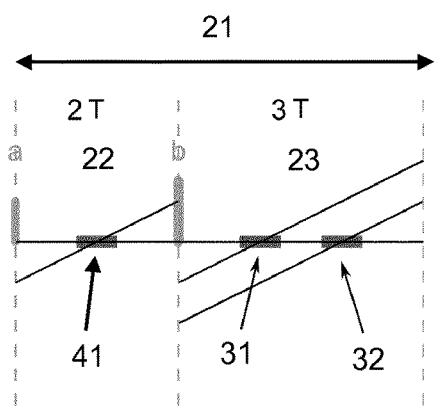
FIG. 4 schematically shows an embodiment of the invention in which three spin echoes are generated during one acquisition block.

In the embodiment shown in FIG. 4, the ratio of the durations of the first and second units 22, 23 is 2:3 such that an additional spin echo 41 is generated in the middle of the first unit 22.

Figure 5:
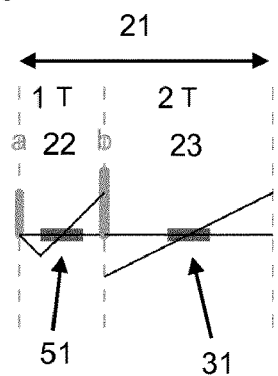
FIG. 5 schematically shows an embodiment of the invention in which one gradient echo and two spin echoes are generated during one acquisition block.

In the embodiment shown in FIG. 5, the ratio of the durations of the first and second units 22, 23 is again 1:2 like in the embodiment of FIG. 2. However, the magnetic field gradient GM is inverted during the first unit 22 such that a gradient echo 51 is generated.

Other combinations of durations of first and second units 22, 23 are conceivable, as long as the durations of the first unit 22 and the second unit 23 are integer multiples of the time interval T respectively. A further condition is that the temporal integral of the magnetic field gradient causing dephasing and rephasing of the transverse magnetization is the same over each interval T.

The invention claimed is:

1. A method of magnetic resonance (MR) imaging of an object placed in an examination volume of a MR device, the method comprising:
  subjecting the object to a steady state spin echo imaging sequence of RF pulses and switched magnetic field gradients (GS, GP, GM), the steady state spin echo imaging sequence comprising a plurality of acquisition blocks, wherein each of the acquisition blocks comprises, in immediate succession:
  i) a first unit starting with an excitation RF pulse radiated toward the object with a duration of the first unit being a first integer multiple of a given time interval T; and
  ii) a second unit starting with a refocusing RF pulse radiated toward the object and comprising a readout magnetic field gradient (GM) and a phase encoding magnetic field gradient (GP); and
  acquiring a plurality of phase-encoded spin echo signals in a sequence of the acquisition blocks, such that at least one of the phase-encoded spin echo signals is acquired in any of the first or second unit at a first integer number of the given time interval T after the refocusing RF pulse and a second integer number of the given time interval T before either an end of said first or second unit or next spin echo signal acquired in said first or second unit, and reconstructing one or more MR images from the acquired spin echo signals.

2. The method of claim 1, wherein the first unit also includes a readout magnetic field gradient (GM) and a temporal integral of the magnetic field gradient (GM) applied during the first and second units correspond to each other so as to produce the phase-encoded spin echo signals.

3. The method of claim 2, wherein the temporal integral of the magnetic field gradient in at least one of direction of the magnetic field gradient (GM) is the same over each time interval T of the acquisition blocks.

4. The method of claim 3, wherein the temporal integral of the magnetic field gradient is the same over each time interval T of the acquisition blocks independently for each gradient direction, except in a direction of the phase-encoding.

5. The method of claim 1, wherein the excitation and refocusing RF pulses each have a flip angle of 20°-90°, preferably 50°.

6. The method of claim 1, wherein a phase difference between the excitation RF pulse and the refocusing RF pulse is at least 30°.

7. The method of claim 1, wherein at least two spin echo signals are acquired during the second unit.

8. The method of claim 1, wherein the first unit further comprises a switched readout magnetic field gradient, with a gradient echo signal being acquired during the first unit.

9. The method of claim 5, wherein the flip angles and/or phases of the RF excitation and refocusing pulses are varied in the sequence comprising the acquisition blocks.

10. The method of claim 1, wherein a repetition time of the imaging sequence is less than 100 ms.

11. The method of claim 6, wherein a phase difference between the excitation RF pulse and the refocusing RF pulse is at least 50°.

12. The method of claim 10, wherein a repetition time of the imaging sequence is less than 20 ms.

13. The method of claim 1, wherein the duration of the second unit is at least twice the duration of the first unit.

14. The method of claim 1, wherein the acquisition blocks are repeatedly applied.

15. The method of claim 14, wherein there is no temporal delay between each of the repeatedly applied acquisition blocks.

16. A magnetic resonance (MR) device comprising at least one main magnet coil for generating a uniform, steady magnetic field within an examination volume, a number of gradient coils for generating switched magnetic field gradients in different spatial directions within an examination volume, at least one RF coil for generating RF pulses within the examination volume and/or for receiving MR signals from an object positioned in the examination volume, a control unit for controlling a temporal succession of RF pulses and switched magnetic field gradients, and a reconstruction unit for reconstructing MR images from the received MR signals, wherein the MR device is arranged to:
  subject the object to a steady state spin echo imaging sequence of RF pulses and switched magnetic field gradients (GS, GP, GM), the steady state spin echo comprising a plurality of acquisition blocks, being repeatedly applied without temporal delay between each repetition, each of the acquisition blocks comprising: i) a first unit starting with an excitation RF pulse radiated toward the object, with a duration of the first unit being a first integer multiple of a given time interval T; and ii) a second unit starting with a refocusing RF pulse radiated toward the object and comprising a readout magnetic field gradient (GM) and a phase encoding magnetic field gradient (GP); and
  acquire a plurality of phase-encoded spin echo signals in a sequence of the acquisition blocks, such that at least one spin echo signal is acquired in any of the first or second unit at a first integer number of the given time interval T after the refocusing rf pulse and a second integer number of the time interval T before either an end of said first or second unit or next spin echo signal acquired in said first or second unit and reconstructing one or more MR images from the acquired spin echo signals.

17. The magnetic resonance (MR) device of claim 16, wherein the first unit also includes a readout magnetic field gradient (GM) and a temporal integral of the magnetic field gradient (GM) applied during the first and second units correspond to each other so as to produce the phase-encoded spin echo signals.

18. The magnetic resonance (MR) device of claim 17, wherein the temporal integral of the magnetic field gradient in at least one of direction of the magnetic field gradient (GM) is the same over each time interval T of the plurality of acquisition blocks.

19. The magnetic resonance (MR) device of claim 18, wherein the temporal integral of the magnetic field gradient is the same over each time interval T of the plurality of acquisition blocks independently for each gradient direction, except in a direction of the phase-encoding.

20. The magnetic resonance (MR) device claim 16, wherein the excitation and refocusing RF pulses each have a flip angle of 20°-90°, preferably 50°.

21. The magnetic resonance (MR) device of claim 16, wherein a phase difference between the excitation RF pulse and the refocusing RF pulse is at least 30°.

22. The magnetic resonance (MR) device of claim 16, wherein at least two spin echo signals are acquired during the second unit.

23. The magnetic resonance (MR) device of claim 16, wherein the duration of the second unit is at least twice the duration of the first unit.

24. The magnetic resonance (MR) device of claim 16, wherein the acquisition blocks are repeatedly applied.

25. The magnetic resonance (MR) device of claim 24, wherein there is no temporal delay between each of the repeatedly applied acquisition blocks.

26. A tangible non-transitory computer readable storage medium that stores instructions, when executed by a processor, cause a magnetic resonance (MR) device to perform a process, the process comprising:

generating a steady state spin echo imaging sequence of RF pulses and switched magnetic field gradients, the steady state spin echo imaging sequence comprising a plurality of acquisition blocks, each of the acquisition blocks comprising: i) a first unit starting with an excitation RF pulse radiated toward a object, with a duration of the first unit being a first integer multiple of a given time interval T; and ii) a second unit starting with a refocusing RF pulse radiated toward the object and comprising a readout magnetic field gradient (GM) and a phase encoding magnetic field gradient (GP), with a duration of the second unit being a second integer multiple of the given time interval T; and acquiring a plurality of phase-encoded spin echo signals in a sequence of the d plurality of acquisition blocks, such that at least one spin echo signal is acquired in any of the first or second unit at a first integer number of the given time interval T after the refocusing rf pulse and a second integer number of the time interval T before either an end of said first or second unit or next spin echo signal acquired in said first or second unit and reconstructing one or more MR image from the acquired spin echo signals.

27. The tangible non-transitory computer readable storage medium of claim 26, wherein the duration of the second unit is at least twice the duration of the first unit.

28. The tangible non-transitory computer readable storage medium of claim 26, wherein the acquisition blocks are repeatedly applied.

29. The tangible non-transitory computer readable storage medium of claim 28, wherein there is no temporal delay between each of the repeatedly applied acquisition blocks.

\* \* \* \* \*